United States Patent [19]

Christenson et al.

[11] 4,071,522

[45] Jan. 31, 1978

[54] TRITIATED O-BENZOYLECGONINE

[75] Inventors: James Gordon Christenson, North Caldwell; Richard R. Muccino, Verona, both of N.J.

[73] Assignee: Hoffmann-La Roche Inc., Nutley, N.J.

[21] Appl. No.: 757,420

[22] Filed: Jan. 6, 1977

[51] Int. Cl.$^2$ ............... A61K 43/00; C07D 471/04
[52] U.S. Cl. ........................ 260/292; 23/230 B; 424/1; 424/12
[58] Field of Search ............ 260/292; 23/230 B; 424/1, 1.5, 12

[56] References Cited

U.S. PATENT DOCUMENTS

| | | | |
|---|---|---|---|
| 3,498,989 | 3/1970 | Sallay | 260/292 |
| 3,555,143 | 1/1971 | Axen et al. | 424/1 |
| 3,709,868 | 1/1973 | Spector | 424/12 |
| 3,888,866 | 6/1975 | Leute et al. | 260/292 |
| 3,917,582 | 11/1975 | Soffer et al. | 260/292 |
| 3,952,091 | 4/1976 | Grunberg et al. | 23/230 B |
| 3,966,744 | 6/1976 | Goldstein et al. | 260/292 |

*Primary Examiner*—Benjamin R. Padgett
*Assistant Examiner*—Christine M. Nucker
*Attorney, Agent, or Firm*—Samuel L. Welt; Jon S. Saxe; George M. Gould

[57] ABSTRACT

The present disclosure relates to tritiated labeled benzoylecgonines. The labeled benzoylecgonines described herein are useful in immunoassays for benzoylecgonine, a metabolite of cocaine.

3 Claims, No Drawings

TRITIATED O-BENZOYLECGONINE

BACKGROUND OF THE INVENTION

Werner and Schmidt, J. Labelled Comp., 5,200 (1969) describe the preparation of tritiated cocaine. As a by-product of this reaction they identified tritiated benzoylecgonine by thin layer chromatography. The total specific activity of all by-products before separation was 820 µCi/mg. Thus the specific acitivity of the by-product tritiated benzoylecgonine was substantially less than that required in a radioimmunoassay.

Bosin et al, Res. Comm. Chem. Path. Pharmacol., ll, 405 (1975) described O-(chlorobenzoyl)ecgonine and O-(m,m-dichlorobenzoyl)ecgonine as intermediates in preparing deuterated benzoylecgonine and cocaine.

DESCRIPTION OF THE INVENTION

The present invention relates to tritiated benzoylecgonine having a specific activity suitable for use as a labeled antigen in radioimmunoassay. In particular the present invention relates to O-benzoylecgonine-$^3$H as well as a novel intermediate useful in the preparation of the aforesaid compound. O-benzoylecgonine-$^3$H is useful in a radioimmunoassay for benzoylecgonine. Such radioimmunoassay requires tritiated labelled antigen having a specific activity of at least 1mCi/mg.

As a means of overcoming this problem, O-(o-iodobenzoyl)ecgonine was prepared by reacting ecgonine with either an o-iodobenzoic anhydride or halide, preferably chloride or bromide. The aforesaid reaction is conveniently carried out at a temperature in the range of about 0° to 20° C, most preferably at about room temperature. An aqueous-organic solvent mixture such as an aqueous ketone, preferably aqueous acetone may be employed as solvent for such reaction.

Conversion of the resultant O-(o-iodobenzoyl)ecgonine to the labeled O-benzoylecgonine can be readily accomplished by catalytic tritiations well known in the art. In a preferred procedure, the O-(o-iodobenzoyl)ecgonine is treated with tritium gas in a closed vessel in the presence of a supported noble metal catalyst, preferably palladium on charcoal and a trialkylamine such as triethylamine. This reaction can be carried out in an inert organic solvent such as a $C_{1-5}$ lower alkanol, preferably methanol. The tritiatium is believed to replace the iodo in the ortho position.

The product O-benzoylecgonine-$^3$H is obtained with a specific activity in excess of 1mCi/mg and thus is useful as a labeled benzoylecgonine in the conduct of immunoassays for the detection of benzoylecgonine, a metabolite of cocaine. Thus, O-benzoylecgonine-$^3$H can be employed in the radioimmunoassay procedure described in U.S. patent application Ser. No. 725,912 entitled "Radioimmunoassay For Benzoylecgonine", filed Sept. 22, 1976, inventor J. Christenson.

The term "halide" is meant to include iodide, bromide, chloride and fluoride; chloride or bromide being preferred, chloride being most preferred.

It is within the skill of the art to prepare acid addition salts, i.e., mineral acid salts such as the hydrochloride salts, sulphates, phosphates, nitrates, etc. or strong organic acid salts such as benzoate, maleate, fumerate, acetate and the like, of the compounds disclosed herein. Such salts are encompassed by the disclosure of the base herein.

EXAMPLE 1

O-(o-iodobenzoyl)ecgonine

A solution of ecgonine (185 mg, 1 mmol) in aqueous acetone (1.5 ml $H_2O$ + 4.5 ml acetone) was stirred for 4 ½ days at room temperature with o-iodobenzoic anhydride (1.43 g, 3 mmol). Evaporation of the solvent in vacuo and trituation of the residue with hexane-ether (1:1, to remove the iodobenzoic acid) gave a solid which after being dissolved in methanol and purified by preparative thin layer chromatography (silica gel, 2 mm; ethyl acetate, acetic acid, water 4:4:1) gave 120 mg of product.

m.p. 183°–185° C.

Nmr and ms data are in agreement with structure.

EXAMPLE 2

O-Benzoylecgonine-$^3$H

O-(o-iodobenzoyl)ecgonine (15 mg, 0.036 mmol) and triethylamine (4.9 µl, 3.64 mg, 0.036 mmol) were dissolved in 0.5 ml of dry methanol in a system having a capacity of 3.5 ml. 10% Palladium on carbon catalyst (5 mg) was added. After evacuation, approximately 2 curies of carrier free tritium gas were admitted (0.036 mmol, about 0.73 ml) and the system was first isolated, then stirred at room temperature 1 hour. Any unreacted tritium gas was then removed and 1 ml of methanol was added. The catalyst was filtered off and the filtrate concentrated to dryness in vacuo. Four such concentrations (to remove labile activity), from 1 ml of methanol each, gave a white residue which was purified by preparative thin layer of chromatography (silica gel, 5% ammonium hydroxide in methanol). 4.1 mg (85.27 mCi) of product were isolated having a specific activity of 20.80 mCi/mg (6.01 mCi/mmol) and a radio chemical purity of 99% (tlc: silica gel; methanol).

We claim:
1. O-(o-iodobenzoyl)ecgonine
2. O-benzoylecgonine-$^3$H having a specific activity greater than 1mCi/mg.
3. The O-benzoylecgonine-$^3$H of claim 2 having a specific activity of about 20.8 mCi/mg.

* * * * *